US009097693B2

(12) United States Patent
Wada et al.

(10) Patent No.: US 9,097,693 B2
(45) Date of Patent: Aug. 4, 2015

(54) SIMPLE ANALYSIS METHOD OF DRUGS

(75) Inventors: Hiroo Wada, Kyoto (JP); Kiyokatsu Jinno, Toyohashi (JP); Yoshihiro Saito, Toyohashi (JP); Youkichi Ohno, Bunkyo-ku (JP); Makiko Hayashida, Bunkyo-ku (JP)

(73) Assignees: SHINWA CHEMICAL INDUSTRIES, LTD., Kyoto (JP); NATIONAL UNIVERSITY CORPORATION TOYOHASHI UNIVERSITY OF TECHNOLOGY, Toyohashi (JP); NIPPON MEDICAL SCHOOL FOUNDATION, Tokyo (JP)

( * ) Notice: Subject to any disclaimer, the term of this patent is extended or adjusted under 35 U.S.C. 154(b) by 685 days.

(21) Appl. No.: 11/886,223

(22) PCT Filed: Mar. 14, 2006

(86) PCT No.: PCT/JP2006/305036
§ 371 (c)(1),
(2), (4) Date: Sep. 13, 2007

(87) PCT Pub. No.: WO2006/098327
PCT Pub. Date: Sep. 21, 2006

(65) Prior Publication Data
US 2008/0193962 A1 Aug. 14, 2008

(30) Foreign Application Priority Data
Mar. 14, 2005 (JP) ................................. 2005-071452

(51) Int. Cl.
| | |
|---|---|
| C12Q 1/02 | (2006.01) |
| G01N 30/16 | (2006.01) |
| A61K 31/465 | (2006.01) |
| G01N 30/88 | (2006.01) |
| G01N 30/00 | (2006.01) |
| G01N 30/06 | (2006.01) |

(52) U.S. Cl.
CPC .............. *G01N 30/16* (2013.01); *A61K 31/465* (2013.01); *G01N 30/88* (2013.01); *G01N 2030/009* (2013.01); *G01N 2030/062* (2013.01); *G01N 2030/167* (2013.01); *G01N 2030/8813* (2013.01)

(58) Field of Classification Search
CPC ................................ A61K 31/465; C12Q 1/02
USPC ................... 73/61.55, 23.41; 435/29
See application file for complete search history.

(56) References Cited

U.S. PATENT DOCUMENTS

| | | |
|---|---|---|
| 5,686,656 A | 11/1997 | Amirav et al. |
| 6,638,346 B1 | 10/2003 | Magni et al. |
| 2004/0091400 A1 | 5/2004 | Wada et al. |

FOREIGN PATENT DOCUMENTS

| | | |
|---|---|---|
| DE | 100 24 443 | 11/2001 |
| JP | 37-5145 | 6/1962 |
| JP | 56-118665 | 9/1981 |
| JP | 62-087856 | 4/1987 |
| JP | 09-325140 | 12/1997 |
| JP | 2004-137341 | 5/2004 |

OTHER PUBLICATIONS

Kataoka, Recent Advances in Solid-Phase Microextraction and Related Techiniques for Pharmaceutical and Biomedical Analysis, Current Pharmaceutical Analysis, Jan. 2005, vol. 1, pp. 65-84.*
Wang et al., Sampling and determination of volatile organic compounds with needle trap devices, Journal of Chromatography A, 1072, 2005, p. 127-135.*
Supplementary European Search Report dated Jul. 10, 2009, issued in corresponding European Application No. 06729070.0-2204.
Wainhaus, et al, "Fast Analysis of Drugs in a Single Hair", J. Am. Soc. Mass. Spectrom, 1998, vol. 9, No. 12, pp. 1311-1320.
Musshoff, et al. "Automated headspace solid-phase dynamic extraction for the determination of amphetamines and synthetic designer drugs in hair samples", J. Chromatography A vol. 958, 2002, pp. 231-238.
Nakahara, "Drug Analysis in Hair—For Monitoring Methamphetamine Abuse History," *Jpn. J. Hosp. Pharm.*, vol. 16, No. 5, pp. 233-247 (1990).
Cirimele et al., "Detection of Amphetamines in Fingernails: An Alternative to Hair Analysis," *Archives of Toxicology*, vol. 70, pp. 68-69 (1995).
Journal of Medical Technology, vol. 39, No. 4, pp. 439-446 (1995).
Pharmacia, vol. 34, No. 9, pp. 889-894 (1998).
Chetiyanukornkul et al., "Hair Analysis of Nicotine and Cotinine for Evaluating Tobacco Smoke Exposure by Liquid Chromatography—Mass Spectrometry," *Biomedical Chromatography*, vol. 18, pp. 655-661 (2004).
Saito et al., "Miniaturized Sample Preparation Needle: A Versatile Design for the Rapid Analysis of Smoking-Related Compounds in Hair and Air Samples," *Journ. of Pharm. and Biomedical Anal.*, 44, pp. 1-7 (2007).

(Continued)

*Primary Examiner* — Taeyoon Kim
*Assistant Examiner* — Tiffany Gough
(74) *Attorney, Agent, or Firm* — Nixon & Vanderhye P.C.

(57) ABSTRACT

The invention provides a method for simple, rapid and inexpensive analysis of drugs such as nicotine and other drugs which are accumulated in biological samples of addictive drugger of tobacco, stimulant drug and the like. The method comprises the steps of introducing the biological sample into an injection needle, inserting the needle into an injector of a chromatograph and injecting a carrier into the needle to conduct chromatography treatment.

7 Claims, No Drawings

(56) References Cited

OTHER PUBLICATIONS

International Search Report for related International Application No. PCT/JP2006/305036 mailed Apr. 18, 2006.

Japanese Office Action for corresponding JP2005-071452, issued Aug. 23, 2010.
Canadian Office Action issued for corresponding Canadian Patent Application No. 2,601,120, dated Mar. 8, 2013.

* cited by examiner

SIMPLE ANALYSIS METHOD OF DRUGS

This application is the National Phase of International Application No. PCT/JP2006/305036, filed Mar. 14, 2006, which designated the U.S. and claims priority to JP 2005-071452, filed Mar. 14, 2005, the entire contents of each of which are hereby incorporated by reference.

FIELD OF THE INVENTION

This invention relates to a simple analysis method of drugs, more particularly to a method for simple and rapid analysis of nicotine and other drugs which are accumulated in biological samples of addictive drugger of tobacco, stimulant drug or the like.

BACKGROUND ART

There have been known that various drugs are accumulated in biological samples including human body such as hair, nail, body hair, skin, bone and the like. Drugs accumulated in biological samples have conventionally been analyzed by a wet process. Namely, biological samples are finely cut, optionally washed, dissolved by alkaline treatment and extracted with a solvent for extracting drugs. The extracted liquid is then subjected to gas chromatography or liquid chromatography, if necessary to mass spectrometry to identify a target drug. The method generally takes at least one to two days and requires considerable labor and expensive apparatus (non-patent documents 1 to 3).

Non-patent document 1 Journal of Medical Technology, Vol. 39, No. 4 (1995), p. 439-446
Non-patent document 2 Pharmacia, Vol. 34, No. 9 (1998), p. 889-894
Non-patent document 3 Biomedical Chromatography 18:655-661 (2004)

DISCLOSURE OF THE INVENTION

Problems to be Solved by the Invention

An object of the present invention is to provide a simple analysis method of drugs, more particularly to a method for simple, rapid and inexpensive analysis of drugs such as nicotine and other drugs which are accumulated in biological samples of addictive drugger of tobacco, stimulant drug or the like.

Means for Solving the Problems

The present invention provides the following method and an injection needle suitably used for the method.

1. A method for analyzing drugs accumulated in a biological sample which comprises the steps of introducing the biological sample into an injection needle, inserting the needle into an injector of a chromatograph and injecting a carrier into the needle to conduct chromatography treatment.
2. The method of the item 1 wherein the biological sample is a solid.
3. The method of the item 1 wherein the biological sample is hair, nail, body hair, skin, bone or the like.
4. The method of any one of the items 1 to 3 wherein the chromatography is gas chromatography, liquid chromatography, supercritical fluid chromatography, inductively-coupled plasma emission spectrometry (ICP), ICP-MS, ion chromatography, size exclusion chromatography, capillary electrophoresis chromatography (CEC), or capillary electrophoresis (CE).
5. The method of any one of the items 1 to 4 wherein the biological sample is introduced into the needle and a solvent is injected into the needle to wash the surface of the biological sample before the carrier is injected to conduct chromatography treatment.
6. The method of any one of the items 1 to 5 wherein the biological sample is introduced into the needle and a solvent is injected into the needle to extract the accumulated drugs in the biological sample before the carrier is injected to conduct chromatography treatment.
7. The method of any one of the items 1 to 6 wherein the biological sample is introduced into the needle and the needle is inserted into the injector of the chromatograph and heat-treated in the injector before the carrier is injected to conduct chromatography treatment.
8. The method of any one of the items 1 to 7 wherein the chromatography is gas chromatography, the biological sample is hair and the accumulated drug is a dependence producing drug.
9. A method for estimating abusion records of a drug of abuse, wherein the method of any one of the items 1 to 8 is used.
10. An injection needle which is used in the method of any one of the items 1 to 8, which has a closed apical end and an aperture in the lateral side near the apical end.

Effects of the Invention

According to the present invention, it is possible to analyze drugs, simply, rapidly and at low cost, such as nicotine and other drugs accumulated in biological samples of addictive drugger, in particular those of tobacco, stimulant drug or the like. Since pre-treatment which was necessary in conventional methods is not necessary in the present invention, it is possible to apply the method of the present invention widely to fields such as judicial trial chemistry, forensic toxicology, clinical toxicology and the like.

BEST MODE FOR CARRYING OUT THE INVENTION

The present invention will now be explained more in detail.
The method of the present invention is characterized in that a biological sample is introduced into an injection needle, the needle is inserted into an injector of a chromatograph and a carrier is injected into the needle to conduct chromatography treatment to analyze drugs accumulated in the biological sample.

The biological sample may be a solid or liquid but preferably a solid because it is easier and simpler to introduce it into an injection needle. Examples of solid samples include hair, nail, body hair, skin, bone and the like.

Most preferred biological sample to which the present invention is applied is hair because it is easy to collect and it is known that various drugs are accumulated in hair. An amount of sample used for the analysis depends on the kind of a target drug but if the sample is hair, the length of the hair is usually 10 to 30 cm, preferably 15 to 25 cm. The weight of the hair is typically about 1 mg per 20 cm.

If necessary, the surface of the collected biological sample may be washed with a solvent before or after the sample is introduced into an injection needle.

Examples of injection needles which can suitably be used in the present invention include those disclosed in JP-A-2004-137341, or those having a closed apical end and an aperture in the lateral side near the apical end. Such needles are commercially available from Shinwa Chemical Industries Ltd., Japan under the trade name of "NeedlEx". The injection needles have an inner diameter of preferably 0.3 to 1 mm, more preferably 0.5 to 1 mm, an outer diameter of preferably 0.5 to 1.2 mm, more preferably 0.7 to 1.2 mm, and a length of preferably 30 to 100 mm, more preferably 50 to 90 mm.

Materials of which the needles are made are not limited to specific ones but preferably heat-resistant and drug-resistant materials such as stainless, titanium, Monel and the like.

Examples of chromatography wherein the present invention is conducted include gas chromatography, liquid chromatography, supercritical fluid chromatography, inductively-coupled plasma emission spectrometry (ICP), ICP-MS, ion chromatography, size exclusion chromatography, capillary electrophoresis chromatography (CEC), capillary electrophoresis (CE) gas chromatography, and capillary electrophoresis (CE) liquid chromatography.

It depends on a target drug but gas chromatography is simple and easy. Conventional chromatograph can be used as it is.

A biological sample is introduced into an injection needle. If the sample is hair, a guide thread such as fishing line is introduced into the needle through an aperture provided in the lateral side near the apical end of the needle to make a loop of the thread outside the inlet of the needle, then, the sample hair is put into the loop and the guide thread is pulled back to introduce the hair sample into the needle. If necessary, hair may be washed with an appropriate solvent such as water or methanol to remove dust on the surface of the hair before or after the hair is introduced into the needle.

The length of hair may be any size as long as it can be introduced into the needle and it is not necessary to finely cut hair. Preferably, the length of the hair sample is almost the same as that of the hair holding portion in the needle to avoid that the sample gets out of the needle through an aperture provided in the lateral side near the apical end of the needle.

The injection needle containing the sample is inserted into an injector of a chromatograph and a carrier is injected into the needle to conduct chromatography treatment. Before the treatment, if necessary, a solvent is injected to wash the surface of the biological sample. For example, methanol, dichloromethane, and methanol, each one ml, are injected in this order to wash the surface of the sample.

A temperature and holding time of the injection needle in the injection portion depend on the kind of a target drug. If nicotine in hair is measured, the sample is hair, the temperature of the injection portion is about 200° C. to about 350° C., preferably about 300° C., and the holding time is about 10 seconds to about 20 seconds, typically about 10 seconds.

According to the present invention, it is possible for certain target drugs to be detected simply by introducing the sample into the needle and inserting and heating the needle into an injection portion of a chromatograph.

However, it is usually preferable to use an appropriate carrier. Examples of such carriers include various eluting solvents such as dichloromethane, chloroform, methanol, ethanol, isopropyl alcohol and the like or inert gas such as nitrogen, helium, hydrogen and the like, and dichloromethane is most preferred for the measurement of nicotine in hair.

According to the present invention, it is also possible for certain target drugs to pre-treat the sample by a derivatizing agent or to introduce a derivatizing agent together with a carrier to convert the target drug to a derivative in the injection needle before it is introduced into a chromatograph.

Examples of the derivatizing agents include trifluoroacetic anhydride, bistrimethylsilyl acetamide, bistrimethylsilyl trifluoroacetamide and the like.

A target drug may typically be identified by a retention time in chromatography and more precisely in combination with mass spectrum measured by a mass spectrometer connected to the chromatograph.

In the present invention, if hair is used as a biological sample, it is possible to estimate abusion records of a dependence producing drug. Drugs taken into a body is accumulated as it is or as a metabolite in the body such as hair. Since hair grows about 1 cm in length a month, it is possible to estimate abusion records of a dependence producing drug for about two years by sampling hair of about 24 cm from the scalp. In addition, if hair is collected and put into an injection needle, and for example, gas chromatography is used, it will take only about 10 minutes from sampling to identification of a target drug. Moreover, the present invention can be conducted easily and at low cost by the use of an injection needle, a chromatograph and a conventional solvent but does not require any remarkably high technique. In addition, hair can easily be collected from a person without pain and easily be stored after collection. Thus, hair is the best sample for the method of the present invention.

Drugs which can be analyzed by the present invention are not limited to specific ones as long as they can be separated by chromatography. Examples include nicotine, cocaine, benzphetamine, phencyclidine, acetyl morphine, LSD, methanephetamine, amphetamine, morphine, deprenyl, THC, ephedrine, phenylpropanolamine, mescaline, 3,4,5-trimethoxyamphetamine, β-phenetylamine, 3,4-methylenedioxymethamphetamine, chloroephedrine, fentanyl, propoxyphene, methoxyphenamine, N-benzylethylamine, dibenzyletylenediamine, phentermine, 2,5-dimethoxy-4-methylamphetamine, 4-bromo-2,5-dimethoxyamphetamine, haloperidol, chlorpromazine, methyl ephedrine, caffeine, thoeophyline, theobromine, chlorphenylamine maleate, dihydrocodeine, diacetylmorphine (heroin), 6-acetylmorphine, amitriptyline, nortriptyline, dothiepin, imipramine, desipramine, clomipramine, doxepin, mianserin, thioridazine, diazepam, flunitrazepam, nitrazepam, oxazepam, temazepam, mianserin, trimipramine, 7-aminoflunitrazepam, bromazepam, clonazepam, triazolam and their metabolites.

The present invention will now be explained more in detail with reference to the following examples.

Example 1

Three 60 mm hairs (about 0.9 mg) were put in a stainless injection needle (inner diameter of 0.5 mm, outer diameter of 0.7 mm, the tip conical part length of 2 mm, the container part length of 80 mm, and one aperture of 0.4 mm in diameter in the lateral side of the end of the container). A syringe was fixed to the needle and methanol, dichloromethane and methanol each one ml were run in this order through the needle to wash the hairs.

Then, the needle was inserted into an injector (at 300° C.) of a gas chromatograph (Agilent, HP-6890) and held for 15 seconds. Then, dichloromethane (25 μL) was injected for desorption and a carrier gas was run. The chromatography was conducted under the following conditions.
Column diameter: 0.25 mm
Column length: 25 m
Column stationary phase: dimethylpolysiloxane (HR-1)
Column temperature: 50° C. to 300° C. (temperature rising: 5° C./min)
Carrier gas: helium Carrier gas flow: 0.9 ml/min
Split ratio: 25:1
Detector: MS (Agilent, HP-5972)

Nicotine was not detected from the hair of nonsmoker but clearly detected from that of smoker.

Example 2

The same procedures as in Example 1 were repeated to detect nicotine in hair except that the amount of hair was changed to 1 mg, 3 mg, 5 mg and 9 mg.

In addition, the same procedures were conducted for a nicotine standard solution (5 ppm, 10 ppm, 20 ppm, 30 ppm and 50 ppm).

The method of the present invention shows good linearity with regard to hair amount and the detection limit is about 0.9 ng/mg (hair).

Example 3

According to the procedures similar to those in Example 1, nicotine content in hair was measured for smokers whose age, tobacco consumption per day, and tobacco brand are different. Three 6 cm hairs (about 0.9 mg) were used for the analysis. The results are shown in Table 1.

TABLE 1

| age of smoker | number of cigarette per day | tobacco brand | nicotine content (mg)(nominal) | nicotine content in hair (ng/mg) |
|---|---|---|---|---|
| 24 | 20 | A | 1.2 | 12.1 |
| 31 | 10 | B | 0.7 | 11.5 |
| 40 | 30 | C | 0.4 | 55.3 |
| 49 | 20 | D | 0.1 | 30.5 |
| 56 | 15 | E | 0.8 | 8.2 |
| 63 | 15 | F | 0.1 | 13.0 |

What is claimed is:

1. A method for analyzing drugs accumulated in a solid biological sample which comprises the steps of introducing the solid biological sample into an injection needle, which has a closed apical end and an aperture in the lateral side near the apical end, inserting the needle into an injector of a chromatograph, heat-treating the inserted needle and injecting a carrier into the needle to conduct chromatography treatment.

2. The method of claim 1 wherein the biological sample is hair, nail, body hair, skin, or bone.

3. The method of claim 1 wherein the chromatography is gas chromatography, liquid chromatography, supercritical chromatography, inductively-coupled plasma emission spectrometry (ICP), ICP-MS, ion chromatography, size exclusion chromatography, capillary electrophoresis chromatography (CEC), or capillary electrophoresis (CE).

4. The method of claim 1 wherein the solid biological sample is introduced into the needle and a solvent is injected into the needle to wash the surface of the biological sample before the carrier is injected to conduct chromatography treatment.

5. The method of claim 1 wherein the solid biological sample is introduced into the needle and a solvent is injected into the needle to extract the accumulated drugs in the biological sample before the carrier is injected to conduct chromatography treatment.

6. The method of claim 1 wherein the chromatography is gas chromatography, the solid biological sample is hair and the accumulated drug is a dependence producing drug.

7. The method of claim 1 further comprising the step of estimating abusion records of a dependence producing drug by sampling the solid biological sample that is hair having a length corresponding to about a two-year period of time.

* * * * *